United States Patent [19]
Bryant et al.

[11] Patent Number: 5,306,277
[45] Date of Patent: Apr. 26, 1994

[54] MONOMER TRANSFER DEVICE

[75] Inventors: Mark Bryant, Auburn; Kirt Case; Todd A. Dawson, both of Warsaw, all of Ind.; Rebecca Gibbs, Greensboro, N.C.; Cary R. Reeves, Leesburg, Ind.

[73] Assignee: Zimmer, Inc., Warsaw, Ind.

[21] Appl. No.: 812,542

[22] Filed: Dec. 23, 1991

[51] Int. Cl.⁵ .......................... A61F 2/32; A61F 2/28; A61M 5/00
[52] U.S. Cl. ........................................ 606/93; 606/92; 623/16; 604/200; 604/187; 604/190; 604/87
[58] Field of Search ...................... 606/92-94, 606/190; 604/87, 187, 89, 92, 141, 190, 191, 200-206, 244, 218; 623/16; 222/541

[56] References Cited

U.S. PATENT DOCUMENTS

| | | | |
|---|---|---|---|
| 1,523,068 | 1/1925 | Hein | 606/93 X |
| 2,764,979 | 10/1956 | Henderson | 222/541 X |
| 3,256,884 | 6/1966 | Hill et al. | 222/541 X |
| 3,306,291 | 2/1967 | Burke | 222/541 X |
| 3,442,424 | 5/1969 | Prussin et al. | 222/541 X |
| 3,458,699 | 7/1969 | Padrta | 222/541 X |
| 4,009,716 | 3/1977 | Cohen | 604/201 X |
| 4,277,184 | 7/1981 | Solomon | 606/93 X |
| 4,331,146 | 5/1982 | Brignola | 604/244 X |
| 4,401,432 | 8/1983 | Schwartz | 604/89 |
| 4,405,249 | 9/1983 | Scales | 606/93 |
| 4,546,767 | 10/1985 | Smith | 606/93 |
| 4,551,135 | 11/1985 | Gorman et al. | 606/93 X |
| 4,576,152 | 3/1986 | Müller et al. | 606/93 |
| 4,625,722 | 12/1986 | Murray | 606/94 X |
| 4,627,434 | 12/1986 | Murray | 606/94 X |
| 4,653,489 | 3/1987 | Tronzo | 606/93 X |
| 4,751,921 | 6/1988 | Park | 606/93 X |
| 4,798,596 | 1/1989 | Mühlbauer | 604/218 |
| 4,872,872 | 10/1989 | Polak | 604/87 X |
| 5,035,348 | 7/1991 | Seifert | 222/541 X |
| 5,071,040 | 12/1991 | Laptewicz, Jr. | 606/93 X |
| 5,100,028 | 3/1992 | Seifert | 222/541 X |
| 5,139,178 | 8/1992 | Arch et al. | 222/326 |
| 5,152,432 | 10/1992 | De Laforcade | 222/541 X |
| 5,181,909 | 1/1993 | McFarlane | 604/87 X |

FOREIGN PATENT DOCUMENTS

| | | | |
|---|---|---|---|
| 2827070 | 1/1980 | Fed. Rep. of Germany | 606/93 |
| 2921565 | 12/1980 | Fed. Rep. of Germany | 606/93 |

Primary Examiner—David Isabella
Assistant Examiner—Elizabeth M. Burke
Attorney, Agent, or Firm—Todd A. Dawson

[57] ABSTRACT

The monomer transfer device of this invention includes a syringe adapted to receive an ampule and adapted for connection to a vacuum source such that with the ampule open within the syringe body, the monomer is vacuumed out of the ampule and into the mixing container. Alternative embodiments accept an unbroken ampule and include an offset designed to break the ampule at its predetermined break point to permit the contents of the ampule to be vacuumed from the ampule and transferred to the mixing container. A small mesh filter or screen may be included to any of the ampule before it reaches the mixing container. Once the ampule is inserted into the syringe, an end cap is connected to close the syringe and maintain any fumes within the syringe. In the alternative embodiments, the end cap acts to force the ampule against the offset so as to cause the ampule to break.

6 Claims, 2 Drawing Sheets

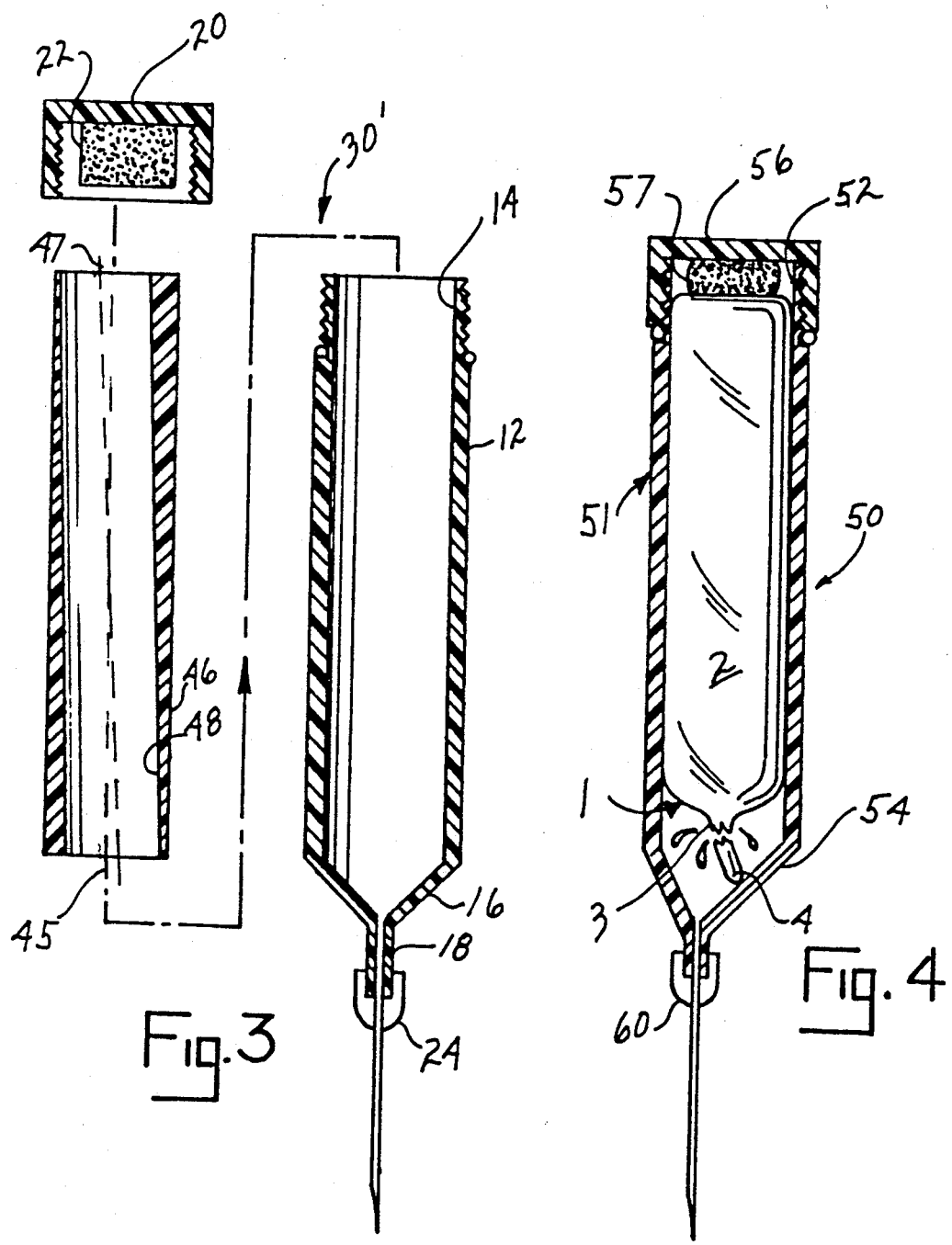

MONOMER TRANSFER DEVICE

FIELD OF THE INVENTION

This invention relates to the field of orthopaedic bone cement mixing devices and has specific relevance to a closed system for transferring the monomer to a closed mixing system.

BACKGROUND OF THE INVENTION

Bone cement, as used in orthopaedic surgery, generally consists of a liquid monomer component mixed with a dry polymer component. The nature of bone cement requires that this mixing take place minutes before its use. Therefore, the bone cement components are usually prepackaged in exact quantities and mixed in the operating room environment.

A problem with bone cement in general is that the fumes given off during the chemical reaction in mixing are highly offensive to operating room personnel. A number of systems have been developed wherein the mixing container is connected to a vacuum port to draw the fumes out of the operating room. It is not uncommon for the liquid monomer, typically packaged in breakable ampules, to be poured into the mixing container before the container is closed and connected to the vacuum port.

SUMMARY OF THE INVENTION

The monomer transfer device of this invention includes a syringe adapted to receive an ampule and adapted for connection to a vacuum source such that with the ampule open within the syringe body, the monomer is vacuumed out of the ampule and into the mixing container. Alternative embodiments accept an unbroken ampule and include an offset designed to break the ampule at its predetermined break point to permit the contents of the ampule to be vacuumed from the ampule and transferred to the mixing container. A small porous filter or screen may be included with any of the syringes to trap small fragments of the glass ampule before they reaches the mixing container. Once the ampule is inserted into the syringe, an end cap is connected to close the syringe and maintain any fumes within the syringe. In the alternative embodiments, the end cap acts to force the ampule against an offset so as to cause the ampule neck to be placed at a critical angle to break the ampule at its neck.

Accordingly, it is an object of the invention to provide for a novel monomer transfer device.

Another object of the invention is to provide for a monomer transfer device which accepts an ampule of monomer and is adapted for connection to a vacuum source to draw the monomer into a mixing container.

Still another object of the invention is to provide for a monomer transfer syringe including an offset to position the ampule at a critical angle and break the monomer ampule at a predetermined location when the ampule is placed within the syringe and the end cap is secured.

Yet another object of the invention is to provide an enclosed monomer transfer device to minimize personal exposure to the monomer fumes.

Further objects of the invention will become apparent upon a reading of the following description taken with the accompanying drawings.

BRIEF DESCRIPTION OF THE DRAWINGS

FIG. 3 is an alternative embodiment of the monomer transfer device of FIG. 2.

FIG. 4 is a third embodiment of the monomer transfer device including an offset between the syringe body and the exit port. A broken ampule is shown for illustrative purposes only.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

An ampule 1 is shown in the figures to fully illustrate and explain the invention. The ampule includes a generally cylindrical body 2 and with a tapered neck portion 3 and a tip 4. The ampule 1 is etched by the manufacturer so as to break easily at a predetermined location on the neck with little fragmentation. To open the ampule, a user grasps the body of the ampule and puts a lateral pressure against the tip. The pressure and the etching allows the ampule to break open in a controlled known manner. Ampules of this type and construction are well known in the industry and are not considered novel to this invention. The specific shape of the ampule may vary by manufacture but will generally include a neck portion which is etched to induce breakage.

Figure 1:
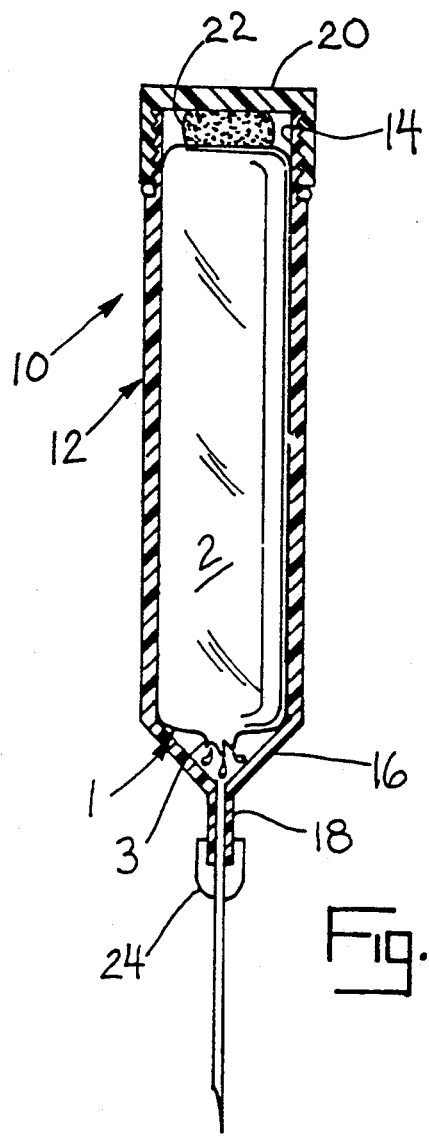
FIG. 1 is a sectional view of the monomer transfer device of the invention illustrated with a broken ampule carried within the syringe.

Referring now to FIG. 1, monomer transfer device 10 includes a generally cylindrical syringe shaped body 12 having an open proximal end 14 and a tapered distal end 16. A tip or nozzle 18 extends from distal end 16 for connection to a hypodermic needle 24 or vacuum tube (not shown). The outer surface of body 12 adjacent end 14 is threaded to accommodate threaded end cap 20. A resilient spacer 22 is connected to the inner surface of end cap 20. In use, the nozzle 18 of device 10 is connected to a vacuum tube leading to a mixing container or is connected to a needle 24 which is inserted through an injection port on the mixing container cover. Needle 24 or the mixing container port may include a filtration system (also not shown) to trap any glass fragments. The tip of an ampule 1 is broken off at the neck 3 and the open ampule is inserted into device 10. The end cap 20 is secured to body 12 such that space 22 pushes against the ampule to urge the ampule toward tapered end 16. The syringe and ampule are positioned as shown in FIG. 1 and a vacuum source (not shown) is turned on to draw the monomer fluid from the ampule. It should be understood that the vacuum source and monomer transfer device 10 are in flow communication with a mixing container (not shown) such that as the monomer liquid is drawn from the ampule and device 10, it is drawn into the mixing container.

Figure 2:
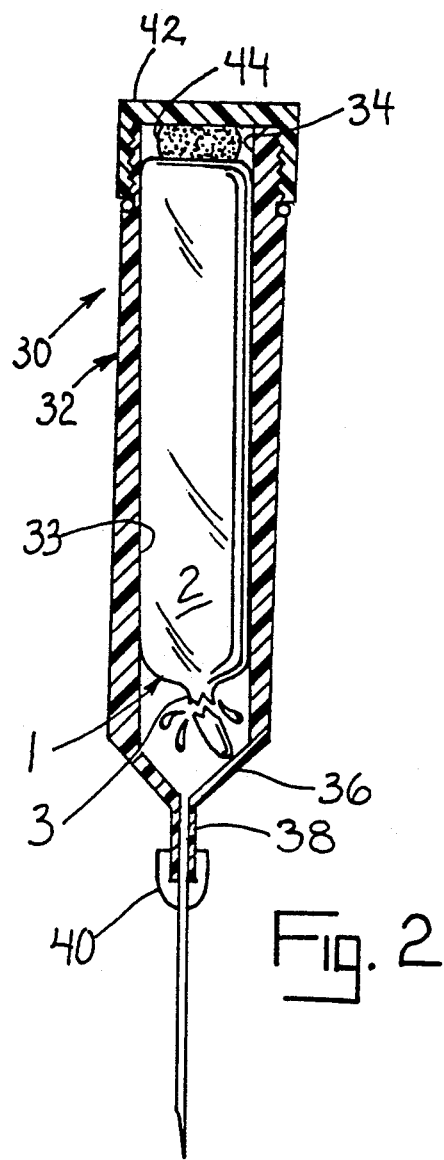
FIG. 2 is a second embodiment of the monomer transfer device wherein the syringe includes an offset. A broken ampule is shown for illustrative purposes only.

A second embodiment is illustrated in FIG. 2. Monomer transfer device 30, as illustrated in FIG. 2, includes a syringe body 32 having an open proximal end 34 and a tapered distal end 36. The tapered distal end 36 terminates in a tip or nozzle 38 for connection to a hypodermic needle 40 or vacuum tubing (not shown). The outer surface of the proximal end 34 is threaded to accommodate a cap 42. Cap 42 carries a resilient pad 44 as shown. As illustrated in the figure, the internal bore 33 of the syringe is offset or angled relative to the outer surface of the syringe body 32. In use, the nozzle 38 of the syringe is connected to a hypodermic needle 40 or to a vacuum tube (not shown). An unbroken ampule 1 is inserted into the internal bore 33 of the syringe such that the tip 4 of the ampule contacts tapered distal end 36. Due to the offset between the internal bore 33 and the body of the syringe 32, the tip 4 of ampule 1 contacts the tapered end 36 at a critical angle. As cap 42 is screwed onto the syringe body 32, pad 44 contacts the ampule and forces it toward the tapered end 36. The force against the ampule, in combination with the critical angle contact between the ampule tip 4 and distal tapered end 36 and the pre-etched neck 3, cause the ampule to break at the neck to release its contents. The term critical angle is used to define an angle which places stress on the ampule such that with minimal force will break the ampule at its predetermined location. An alternative embodiment 30' of the invention of FIG. 2 is illustrated in FIG. 3. In FIG. 3, the syringe body and cap are substantially similar to the syringe body 12 and cap 20 of figure 1, therefore, like numbers are used between FIGS. 1 and 3 to connote similar structure and function. As illustrated in figure 3, a sleeve 46 is inserted into body 12 of the syringe. The sleeve 46 includes an inner throughbore 48 for accommodating an ampule. The longitudinal axis 47 of the throughbore 48 is offset relative to the longitudinal axis 45 of the sleeve such that when the sleeve is positioned within body 12, the resultant monomer transfer device 30' is substantially similar in function and operation to the monomer transfer device 30 of FIG. 2 and functions consistent with the above description. The advantage of the device 30' of FIG. 3 would be a reduction in cost in that stock syringe bodies could be obtained and fitted with the sleeve 46.

A third embodiment of the invention is illustrated in figure 4. The monomer transfer device 50 of FIG. 4 includes a syringe body 51 having a proximal open end 52 and a tapered distal end 54. The outer surface of the syringe body 51 adjacent the proximal end is threaded to accommodate a threaded cap 56. Cap 56 carries a resilient pad 57. The distal end of the syringe 51 terminates in a tip or nozzle 58 for accommodating a hypodermic needle 60 or vacuum tube (not shown). As illustrated, the nozzle 58 is offset from the longitudinal center of the syringe body. In use with the monomer transfer device 50 connected to a hypodermic needle or vacuum tubing, an unbroken ampule 1 is inserted into the syringe body 51. The tip 4 of ampule 1 contacts the tapered distal end 54 of the syringe body at a point other than the nozzle 58 since nozzle 58 is offset from the center of the syringe body. The tip contacts the distal tapered end at a critical angle. Again due to the critical angle contact between the ampule tip 4 and the distal tapered end 54 and the force applied through continued tightening of the cap 56 compressing pad 57, the ampule 1 breaks along its etch line at its neck. Once the ampule is broken open, the contents may be drawn out under vacuum in a manner consistent with the above disclosure.

Since the syringe bodies of FIGS. 1-4 are closed during the entire process, the fumes from the monomer are contained within the syringe or drawn out by the vacuum source. In either case the fumes from the monomer are substantially contained. Further, in the embodiments of FIGS. 2-4, the ampule may be inserted intact and broken within the syringe bodies thereby eliminating any chance of injury caused during opening the ampule.

Figure 5:
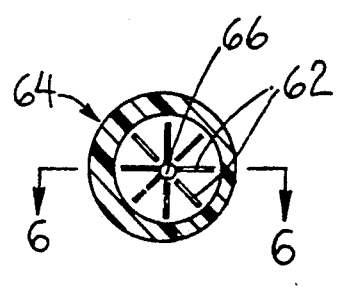
FIGS. 5 and 6 are cross sectionals of an alternative embodiment of the invention.
Figure 6:
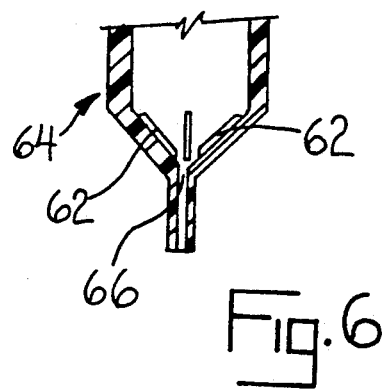

To prevent the blockage of the nozzles of the syringe bodies of FIGS. 1-4, it may be necessary to provide a plurality of axially extending ribs in the distal end of the syringe bodies. An example of such is illustrated in FIGS. 5 and 6 and is applicable to each of the embodiments shown above. Ribs 62 extend upwardly from the distal end of the syringe 64 and are axially spaced. In use, broken tip of the ampule would rest on the ribs 62 to prevent blockage of the nozzle opening 66.

It may be necessary to provide a vent opening through the caps with a one-way valve to allow air to flow into the transfer devices after the vacuum is initialed to permit fluid flow from the transfer device.

It should be understood that it may be necessary to place a filter or screen in line with the hypodermic needle or vacuum tube to collect any glass fragments which may have broken off of the ampule during insertion or opening of the ampule. It should also be understood that after use, the syringe and ampule should be discarded.

It should also be understood that the invention is not to be limited to the above disclosure but may be modified within the scope of the appended claims.

We claim:

1. A monomer transfer device for connection to a bone cement mixing container for transferring a liquid monomer contained within an ampule to the mixing container, the ampule including an ampule body having a neck portion and a tip portion, the neck portion being predisposed to break at a predetermined location to separate the tip from the ampule body, said monomer transfer device comprising a generally cylindrical body having an open end and a tapered end, a nozzle extending from the tapered end, said generally cylindrical body including a longitudinal bore extending from said open end to said tapered end for accommodating the ampule body, a cap for connection to said generally cylindrical body for capping the open end of the generally cylindrical body, said generally cylindrical body configured for carrying said ampule, said nozzle adapted for connection to conduit means for passing said liquid monomer from the body through the nozzle into said mixing container, said monomer transfer device further including transferring means for causing the monomer to flow from the ampule into the mixing container, wherein said cap includes a biasing member pad on an inner surface of said cap for compressively contacting the ampule to urge said ampule toward said tapered end.

2. The monomer transfer device of claim 1 wherein a longitudinal bore of said generally cylindrical body is angled relative to said generally cylindrical body such that the tip of the ampule contacts said tapered end at a critical angle, wherein said biasing member pad urges said ampule against said tapered end as said cap is connected to said generally cylindrical body, the tapered end and the biasing member pad and the angle of the longitudinal bore constitute means for causing said ampule to separate the tip from the ampule body.

3. The monomer transfer device of claim 1 wherein said nozzle is offset from a longitudinal axis of said generally cylindrical body such that said tip of said ampule contacts said tapered end of the generally cylindrical body at a critical angle.

4. The monomer transfer device of claim 2 wherein said generally cylindrical body includes a tube insert extending substantially an entire length of the generally cylindrical body, said tube insert defining an outer tube having a longitudinal axis generally parallel to said generally cylindrical body and an inner tube having a longitudinal axis at an angle relative to said generally cylindrical body said inner tube constituting said longitudinal bore of said generally cylindrical body.

5. The monomer transfer device of claim 1 further including a plurality of spaced apart ribs extending from the tapered end toward the open end of generally cylindrical body.

6. The monomer transfer device of claim 1 wherein said transferring means is a vent opening formed in said cap.

* * * * *